United States Patent [19]

Sainsbury et al.

[11] Patent Number: 5,185,360
[45] Date of Patent: Feb. 9, 1993

[54] DIHYDROINDENOINDOLE COMPOUNDS AND METHODS FOR USING THE SAME

[75] Inventors: Malcolm Sainsbury, Bristol, United Kingdom; Howard G. Shertzer, Cincinnati, Ohio

[73] Assignees: University of Bath, Bath, England; University of Cincinnati, Cincinnati, Ohio

[21] Appl. No.: 709,656

[22] Filed: Jun. 3, 1991

Related U.S. Application Data

[63] Continuation of Ser. No. 542,312, Jun. 22, 1990, abandoned.

[30] Foreign Application Priority Data

Jun. 22, 1989 [SE] Sweden ................. 8902273

[51] Int. Cl.$^5$ ................. C07D 209/94; C07D 209/70; A61K 31/40
[52] U.S. Cl. ..................... 514/410; 548/420
[58] Field of Search ............ 548/420; 514/410

[56] References Cited

U.S. PATENT DOCUMENTS 3,478,208  11/1969  Horrocks et al. ............... 250/71.5
3,714,148  1/1973   Okamoto et al. ............... 260/239 D

FOREIGN PATENT DOCUMENTS 62-56471  3/1987  Japan .

OTHER PUBLICATIONS

Horrocks et al, J. Chem. Phys. 47, pp. 3241–3247, (1967).
Horrocks et al, J. Chem. Phys. 49, pp. 2907–2912 (1968).
Horrocks, J. Chem. Phys. 49, pp. 2913–2917 (1968).
Suzuki et al, Chem. Abstracts 107, No. 39609h, (1987).
Eisch et al, Tetrahedron Letters 20, pp. 1647–1650, (1976).
Kempter, et al, J. Prakt. Chem. 18, pp. 39–46, (1962).
Kempter, et al, Chem. Abstracts 57, p. 15052, (1962).
Kempter, et al, Chem. Abstracts, 7th Collective Subject index, p. 11655, (1969).
Letcher, et al, J. Chem. Soc. Chem. Commun., pp. 1602–1603 (1987).
Bill, et al, Heterocycles 20, pp. 2433–2436, (1983).
Bill, et al, Chem. Abstracts 100, No. 191091w (1984).
Buu-Hoi, et al, J. Chem. Soc. 2, pp. 2225–2228, (1952).
Seka, et al, Ber. Duetsch. Chem. Gef. 75B, pp. 1730–1738, (1942).
Schertzer, et al, Fd. Chem. Toxic. 26, pp. 517–522, (1988).
Schertzer, et al, FASEB Journal 2, p. A407, No. 648, (1988).
Schertzer, et al, Chem. Abstracts 109, p. 248, No. 224224h, (1988).
Beilsteins Handbuch der Organischen Chemie 20, pp. 4160, 4204 and 4216, (1978).

Primary Examiner—Joseph Paul Brust
Attorney, Agent, or Firm—White & Case

[57] ABSTRACT

Compounds of the formula

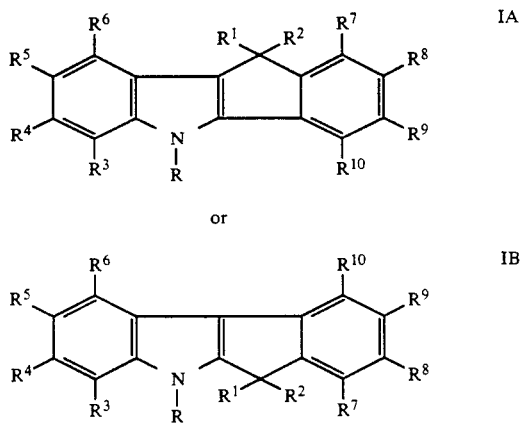

wherein R is hydrogen or a lower alkyl group,
$R^1$ and $R^2$ are independently selected from hydrogen or a lower alkyl group, $R^3$, $R^4$ and $R^6$ are independently selected from hydrogen, halogen or a lower alkyl group,
$R^5$ is hydrogen, hydroxy, halogen, a lower alkyl group, a lower alkoxy group, a mono- or di-lower alkylamino group, $NH_2$ or $NR^{11}COR^{12}$,
$R^7$, $R^8$, $R^9$ and $R^{10}$ are independently selected from hydrogen, hydroxy, a lower alkyl group, a lower alkoxy group, a mono- or di-lower alkylamino group, $NH_2$ or $NR^{11}COR^{12}$,
$R^{11}$ is a hydrogen or a lower alkyl group,
$R^{12}$ is a lower alkyl group, with the proviso that when R is hydrogen then at least one of the substituents $R^1$ to $R^{10}$ is not hydrogen, or a salt thereof, are useful as antioxidants, within the medical and non-medical field, and that when R is hydrogen, methyl or neopentyl in formula IA, then at least one of $R^1$ to $R^{10}$ is not hydrogen. Many of the compounds of formula IA and IB are new and various methods for preparing them are described.

23 Claims, No Drawings

DIHYDROINDENOINDOLE COMPOUNDS AND METHODS FOR USING THE SAME

This application is a continuation of application Ser. No. 07/542,312, filed on Jun. 22, 1990, now abandoned.

DESCRIPTION

1. Field of the Invention

The present invention relates to a novel type of hydrophobic antioxidant, based on the indenoindole structure, which is highly efficient in reducing, i.e. quenching, free radicals in lipids or lipid biphases, thereby, terminating the lipid peroxidation process and preventing conditions and diseases initiated by this, or related processes. The invention also relates to compositions, especially pharmaceutical compositions, containing at least one compound of the invention, or a salt thereof, especially a therapeutically acceptable salt thereof, as active ingredient. In a further aspect, the invention relates to processes for the preparation of such compounds and to the use of the active compounds in medical therapy as well as non-medical applications. Especially important in non-medical applications would be the use in controlling or terminating free-radical medicated processes.

2. Background of the Invention

Some biological processes generate more or less stable intermediates that contain an unpaired electron, which can either be donated, or paired with an additional electron from the surroundings. Such intermediates are called free radicals, and they may be the products of various enzymatic and non-enzymatic reactions, some of which are vital for body functions, e.g. reduction of ribonucleoside diphosphates for DNA synthesis and the generation of prostaglandins in the prostaglandin synthase reaction. The latter is essential for inflammatory response following cell injury, and a number of other functions. Other radical reactions include the myeloperoxidase reaction in neutrophils and macrophages which destroy bacteria and other invading particles, and the electron transport in the mitochondrial respiratory chain. Most organisms contain chemical antioxidants such as α-tocopherol (vitamin E) ascorbic acid and different radical and peroxide-inactivating enzymes, e.g. superoxide dismutase, catalase and glutathione peroxidase.

Free radicals of various types are becoming increasingly associated with a broad range of conditions and diseases such as ischemic or reperfusion injury, thrombosis and embolism, atherosclerosis, allergic/inflammatory conditions such as bronchial asthma and rheumatoid arthritis, conditions related to Parkinson's disease, Alzheimer's disease or ageing, cataract, diabetes, neoplasms and toxicity of anti-neoplastic or immuno suppresive agents and chemicals. One possible explanation for these conditions and diseases is that, for unknown reasons, the endogeneous protecting agents against radical damage are not sufficiently active to protect the tissue against radical damage. Lipid peroxidation caused by excess generation of radicals may constitute one significant damaging pathway in the above conditions and diseases. Administration of additional antioxidants, which inhibit radical reactions, e.g. lipid peroxidation, would thus provide a way of preventing or curing the above conditions and diseases. The present invention describes new antioxidants of the indenoindole type that fulfils both the requirement to accumulate in membranes, i.e. they are sufficiently hydrophobic, and they are potent inhibitors of lipid peroxidation. These new antioxidants compare favourably with other antioxidants, e.g. α-tocopherol.

The compounds of the present invention may also be used in non-medical applications to stabilise compounds susceptible to oxidative deterioration, for example in skin care products, food additives, food preservation, and for preservation of other products. The present invention extends to both a method of stabilisation using the indenoindoles and the resulting stabilised compositions.

PRIOR ART

Some of the compounds of the invention have been described before.

5,10-Dihydroindeno[1,2-b]indole and 5,6-dihydroindeno[2,1-b]indole are described in FASEB J. 2, A 407 (1988). The abstract describes compounds inhibiting lipid peroxidation in NADPH-fortified mouse liver microsomes initiated with $CCl_4$. Further, 5,10-dihydroindeno[1,2-b]indole is described as a potent inhibitor of lipid peroxidation in Fd Chem. Toxicol. 26, 517 (1988). The Japanese patent application 194916/85 (56471/87) discloses 2-hydroxy- and 2-methoxy-substituted-5,10-dihydroindeno[1,2-b]indoles.

5-Methyl-5,10-dihydroindeno[1,2-b]indole and 5-neopentyl-5, 10-dihydroindeno[1,2-b]indole are known as scintillators by J Chem. Physics, 49, (7), 2906 (1968).

8-Methyl-, 8-methoxy-, 8-ethoxy-5,10-dihydroindeno[1,2-b]indole are disclosed in J. Prakt. Chemie, 4, (18), 41 (1962).

7-Chloro-5,10-dihydroindeno[1,2-b]indole is disclosed as an isolated intermediate in a process for preparing dibenzazocine derivatives in U.S. Pat. No. 3,714,148.

3-Isopropyl-, 3-chloro-, 8-bromo-3-methyl-, 3-chloro-8-methyl-, 8-bromo-3-chloro-, 3,8-dimethyl-5,10-dihydro-indeno[1,2-b]indole are disclosed in J. Chem. Soc. 2, 2225 (1952).

DISCLOSURE OF INVENTION

It has been found that compounds with the indenoindole structures of formula IA (DHII) and IB (iso-DHII) are effective as inhibitors of the lipid peroxidation process. The following compounds of formulae IA and IB are particularly useful as antioxidants

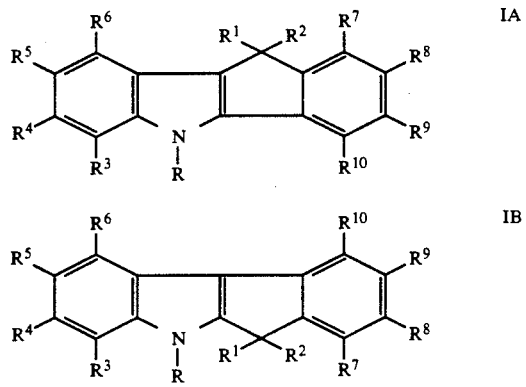

wherein R is hydrogen or a lower alkyl group,
R¹ and R² are independently selected from hydrogen or a lower alkyl group, R³, R⁴ and R⁶ are independently selected from hydrogen, halogen or a lower alkyl group, R⁵ is hydrogen, hydroxy, halogen, a lower alkyl group, a lower alkoxy group, a mono- or di-lower alkyl amino group, NH₂ or

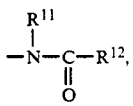

R⁷, R⁸, R⁹ and R¹⁰ are independently selected from hydrogen, hydroxy, a lower alkyl group, a lower alkoxy group, a mono- or di-lower alkylamino group, NH₂ or

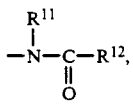

R¹¹ is a hydrogen or a lower alkyl group,
R¹² is a lower alkyl group,
with the following provisos that:
 i) when R is hydrogen in formulae IA or IB then at least one of the substituents R¹ to R¹⁰ is not hydrogen,
 ii) when R, R¹, R², and R¹⁰ are hydrogen and R⁷ and R⁹ are lower alkyl and R³, R⁴, R⁵ and R⁶ are hydrogen or lower alkyl or R⁵ is hydroxy or lower alkoxy in formula IA then R⁸ is not hydroxy, or a salt thereof.

The novel compounds of the present invention have either the formulae IA or IB

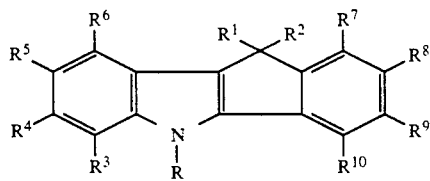

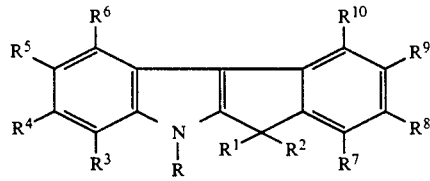

wherein R is hydrogen or a lower alkyl group,
R¹ and R² are independently selected from hydrogen or a lower alkyl group, R³, R⁴ and R⁶ are independently selected from hydrogen, halogen or a lower alkyl group,
R⁵ is hydrogen, hydroxy, halogen, a lower alkyl group, a lower alkoxy group, a mono- or di-lower alkylamino group, NH₂ or

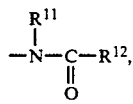

R⁷, R⁸, R⁹ and R¹⁰ are independently selected from hydrogen, hydroxy, a lower alkyl group, a lower alkoxy group, a mono- or di-lower alkylamino group, NH₂ or

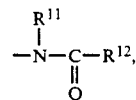

R¹ is a hydrogen or a lower alkyl group,
R¹² is a lower alkyl group,
with the following provisos that:
 i) when R is hydrogen in formula IB then at least one of R¹ to R¹⁰ is not hydrogen,
 ii) when R is hydrogen, methyl or neopentyl in formula IA then at least one of R¹ to R¹⁰ is not hydrogen,
 iii) when R, R¹, R² and R¹⁰ are hydrogen and R⁷ and R⁹ are lower alkyl and R³, R⁴, R⁵ and R⁶ are hydrogen or lower alkyl or R⁵ is hydroxy or lower alkoxy in formula IA then R⁸ is not hydroxy or methoxy,
 iv) when R⁴ is chloro in formula IA then at least one of R¹ to R¹⁰ is not hydrogen,
 v) when R⁹ is ethyl, i-propyl, methoxy or ethoxy in formula IA then at least one of R to R⁸ or R¹⁰ is not hydrogen,
 vi) when R⁹ is ethyl in formula IA then R⁵ is not methyl,
 vii) when R⁹ is methoxy or ethoxy in formula IA then R³ and R⁶ are not methyl simultaneously,
 viii) when R⁸ is methyl in formula IA then R³ and R⁹ are not methyl simultaneously or at least one of R to R⁷, R⁹ or R¹⁰ are not hydrogen,
 ix) when R⁵ is bromo in formula IA then at least one of R to R⁴, R⁶ to R¹⁰ is not hydrogen, or a salt thereof.

The following compounds of formulae IA and IB which are effective as inhibitors of the lipid peroxidation process are particularly useful as antioxidants in the medical therapy

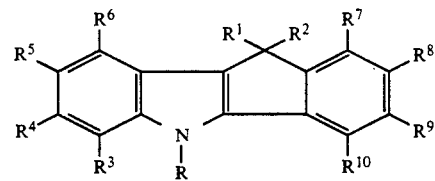

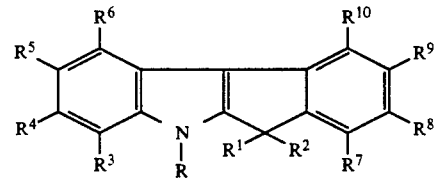

wherein R is hydrogen or a lower alkyl group,
R¹, R² are independently selected from hydrogen or a lower alkyl group, R³, R⁴ and R⁶ are independently selected from hydrogen, halogen or a lower alkyl group,
R⁵ is hydrogen, hydroxy, halogen, or lower alkyl group or a lower alkoxy group, a mono- or di-lower alkyl amino group, NH₂ or

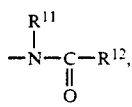

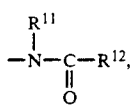

$R^7$, $R^8$, $R^9$ and $R^{10}$ are independently selected from hydrogen or hydroxy, a lower alkyl group, a lower alkoxy group, a mono- or di-lower alkyl amino group, $NH_2$ or $R^{11}$ is a hydrogen or a lower alkyl group, $R^{12}$ is a lower alkyl group, with the following provisos that:
i) when R is hydrogen then at least one of the substituents $R^1$ to $R^{10}$ is not hydrogen,
ii) when R, $R^1$, $R^2$ and $R^{10}$ are hydrogen and $R^7$ and $R^9$ are lower alkyl and $R^3$, $R^4$, $R^5$ and $R^6$ are hydrogen or lower alkyl or $R^5$ is hydroxy or lower alkoxy in formula IA then $R^8$ is not hydroxy,
or a pharmaceutically acceptable salt thereof.

The indenoindole and iso-indenoindole structures of the present invention have the following numbering in the rings.

INDENOINDOLE STRUCTURE

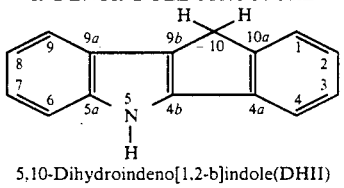

5,10-Dihydroindeno[1,2-b]indole(DHII)

ISO-INDENOINDOLE STRUCTURE

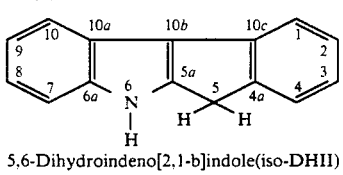

5,6-Dihydroindeno[2,1-b]indole(iso-DHII)

The term "lower" in the definition of substituents in the compound of the present invention means a number of carbon atoms not more than 6, preferably not more than 4.

The lower alkyl group in the definition of R, $R^1$, $R^2$, $R^3$, $R^4$, $R^5$, $R^6$, $R^7$, $R^8$, $R^9$, $R^{10}$, $R^{11}$ and $R^{12}$ is an alkyl group having 1–6 carbon atoms, preferably 1–4 carbon atoms e.g. methyl, ethyl, n-propyl, isopropyl, n-butyl, secbutyl or tert-butyl, especially preferred are methyl and ethyl.

The lower alkoxy group in the definition of $R^5$, $R^7$, $R^8$, $R^9$ and $R^{10}$ is an alkoxy group having 1–6 carbon atoms, preferably 1–4 carbon atoms e.g. methoxy, ethoxy, n-propoxy, iso-propoxy, n-butoxy, sec-butoxy or tert-butoxy, especially preferred are methoxy and ethoxy.

Halogen in the definition of $R^3$, $R^4$, $R^5$ and $R^6$ is chlorine, bromine, iodine or fluorine.

The mono- or di-lower alkylamino group in the definition of $R^5$, $R^7$, $R^8$, $R^9$ and $R^{10}$ include methylamino, dimethylamino, ethylamino, diethylamino, propylamino, dipropylamino, butylamino, dibutylamino, preferred are ethylamino or diethylamino.

Preferred groups of compounds of the invention are those wherein $R^8$ is a mono- or di-lower alkylamino group, particularly ethylamino and diethylamino, and those wherein $R^3$ and/or $R^5$ is a lower alkyl group, particularly methyl, and those wherein $R^5$ is lower alkoxy group, particularly methoxy, and those wherein $R^8$ is $NR^{11}COR^{12}$ particularly NH-acetyl.

Other preferred groups of compounds of the invention are those wherein
i) $R^8$ is mono- or di-lower alkylamino, preferably ethylamino or diethylamino and R, $R^1$ to $R^7$ and $R^9$ to $R^{10}$ are hydrogen;
ii) $R^5$ is a lower alkoxy, preferably methoxy and R, $R^1$ to $R^4$ and $R^6$ to $R^{10}$ are hydrogen;
iii) $R^3$ and/or $R^5$ are lower alkyl, preferably methyl and R, $R^1$, $R^2$, $R^4$, $R^6$ to $R^{10}$ are hydrogen;
iv) $R^8$ is $NHCRO^{14}$, preferably NH-acetyl.

Preferred compounds of the formulae IA and IB are the following;

5,10-Dihydro-10,10-dimethylindeno[1,2-b]indole
5,10-Dihydro-8-methylindeno[1,2-b]indole
5,10-Dihydro-8-isopropylindeno[1,2-b]indole
5,10-Dihydro-6-chloroindeno[1,2-b]indole
5,10-Dihydro-8-fluoroindeno[1,2-b]indole
5,10-Dihydro-8-methoxyindeno[1,2-b]indole
5,10-Dihydro-10-methylindeno[1,2-b]indole
5,10-Dihydro-6,8-dimethylindeno[1,2-b]indole
5,10-Dihydro-2-methoxy-1,3,6,8-tetramethylindeno[1,2-b]indole
5,10-Dihydro-2-methoxy-1,3-dimethyl-8-isopropylindeno[1,2-b]indole
5,10-Dihydro-2-hydroxy-1,3-dimethyl-8-isopropylindeno[1,2-b]indole
5,10-Dihydro-2,8-dimethoxy-1,3-dimethylindeno[1,2-b]indole
5,10-Dihydro-8-tert.butylindeno[1,2-b]indole
5,10-Dihydro-2-ethylaminoindeno[1,2-b]indole
5,10-Dihydro-2-diethylaminoindeno[1,2-b]indole
5,10-Dihydro-8-methoxy-7,9-dimethylindeno[1,2-b]indole
5,10-Dihydro-8-hydroxy-7,9-dimethylindeno[1,2-b]indole
5,10-Dihydro-8-methoxy-6-methylindeno[1,2-b]indole
5,6-Dihydro-9-methoxyindeno[2,1-b]indole
5,6-Dihydro-9-isopropylindeno[2,1-b]indole
5,6-Dihydro-9-fluoroindeno[2,1-b]indole
5,6-Dihydro-9-tert.butylindeno[2,1-b]indole
5,10-Dihydro-2-(N-acetyl-N-ethyl)aminoindeno[1,2-b]indole
5,10-Dihydro-2-aoetamidoindeno[1,2-b]indole
5,10-Dihydro-6-isopropylindeno[1,2-b]indole
5,10-Dihydro-6-isopropyl-8-methoxyindeno[1,2-b]indole
5,10-Dihydro-4,6-dimethyl-8-methoxyindeno[1,2-b]indole
5,10-Dihydro-8-diethylamino-6-methylindeno[1,2-b]indole
5,10-Dihydro-8-ethylamino-6-methylindeno[1,2-b]indole
5,10-Dihydro-8-methoxy-6,10,10-trimethylindeno[1,2-b]indole
5,10-Dihydro-9-diethylamino-6-methylindeno[1,2-b]indole
5,10-Dihydro-9-methoxy-6-methylindeno[1,2-b]indole 5,10-Dihydro-7,9-dimethoxyindeno[1,2-b]indole
5,10-Dihydro-8-diethylamino-6,10,10-trimethylindeno[1,2-b]indole
5,10-Dihydro-4-diethylaminoindeno[1,2-b]indole
5,10-Dihydro-3-hydroxy-2,4-dimethylindeno[1,2-b]indole
5,10-Dihydro-3-methoxy-2,4-dimethylindeno[1,2-b]indole
5,10-Dihydro-7-hydroxy-6,8-dimethylindeno[1,2-b]indole
5,10-Dihydro-7-methoxy-6,8-dimethylindeno[1,2-b]indole
5,10-Dihydro-2,8-dihydroxy-1,3,7,9-tetramethylindeno[1,2-b]indole
5,10-Dihydro-2,8-dimethoxy-1,3,7,9-tetramethylindeno[1,2-b]indole
5,10-Dihydro-8-hydroxy-7,9-ditert.butylindeno[1,2-b]indole
5,10-Dihydro-8-methoxy-7,9-ditert.butylindeno[1,2-b]indole
5,6-Dihydro-9-methoxy-7-methylindeno[2,1-b]indole
5,6-Dihydro-9-diethylamino-7-methylindeno[2,1-b]indole
5,6-Dihydro-2-hydroxy-1,3-dimethylindeno[2,1-b]indole
5,6-Dihydro-2-methoxy-1,3-dimethylindeno[2,1-b]indole
5,6-Dihydro-3-hydroxy-2,4-dimethylindeno[2,1-b]indole
5,6-Dihydro-3-methoxy,2,4-dimethylindeno[2,1-b]indole
5,6-Dihydro-9-hydroxy-8,10-dimethylindeno[2,1-b]indole
5,6-Dihydro-9-methoxy-8,10-dimethylindeno[2,1-b]indole
5,6-Dihydro-8-hydroxy-7,9-dimethylindeno[2,1-b]indole
5,6-Dihydro-8-methoxy-7,9-dimethylindeno[2,1-b]indole
5,6-Dihydro-3-acetamidoindeno[2,1-b]indole
5,6-Dihydro-3-(N-acetyl-N-ethyl)aminoindeno[2,1-b]indole
5,6-Dihydro-9-acetamidoindeno[2,1-b]indole
5,10-Dihydro-8-acetamidoindeno[1,2-b]indole
5,6-Dihydro-1-diethylaminoindeno[2,1-b]indole
5,6-Dihydro-3-diethylaminoindeno[2,1-b]indole
5,6-Dihydro-3-hydroxy-2,4-dimethylindeno[2,1-b]indole Some of the preferred compounds are known and described in the prior art.

The compounds having formulae IA and IB can exist either as such or as pharmaceutically acceptable salts.

PHARMACEUTICAL PREPARATIONS

According to the present invention the compounds of the formulae IA or IB will normally be administered orally, rectally, dermally or by injection, in the form of pharmaceutical preparations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration. Dermal administration would normally utilize 0.1-5% by weight of the active ingredient in a suitable vehicle.

To produce pharmaceutical preparations containing a compound of the formula I in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or poly-vinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or poly-ethylene glycol. Hard gelatine capsules may contain granules of the active substance using either the abovementioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethyl-cellulose as a thickening agent or other excipients known to the man skilled in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutical treatment of humans are about 0.01-100 mg/kg body weight at peroral administration and 0.001-100 mg/kg body weight at parenteral administration.

METHOD OF PREPARATION

The compounds of the invention may be prepared as outlined below, however, the invention is not limited to these methods, the compounds may be prepared by processes described in known art.

a. 5,10-Dihydroindeno[1,2-b]indole (DHII, IA) and analogues containing functional groups on the atoms of the benzenoid rings and/or substiutents at C-10, such as alkyl (e.g. methyl, ethyl, isopropyl), or alkoxy (e.g. methoxy, or ethoxy) may be prepared by the Fischer indole synthesis.

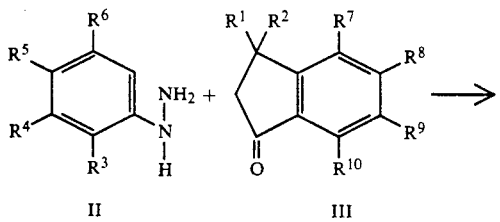

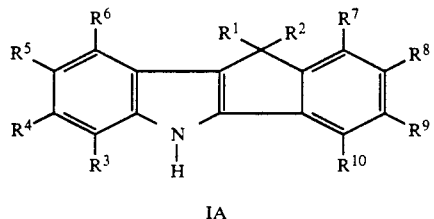

1-Indanone (III), or an equivalent starting material, with appropriate functional group substitution in the benzenoid ring and at C-3, may be reacted with phenylhydrazines (II) either as the free base, or as a salt, preferably the hydrochloride, $R^1$, $R^2$, $R^3$, $R^4$, $R^5$, $R^6$, $R^7$, $R^8$, $R^9$ and $R^{10}$ have the same meaning given under formula IA above. Normally the reactants are dissolved in a solvent preferably an alcoholic solvent such as ethanol or propanol. In some cases heat is not required, whereas in others it is necessary to heat the reaction mixture at reflux for up to 1 hour, or more. The phenylhydrazone product can be isolated by dilution of the reaction mixture with water and separated by filtration, or by extraction with a suitable solvent. Further purification is achieved by crystallization or by chromatography. In the last case column chromatography on silica is satisfactory, and a range of eluting solvents may be used.

Cyclisation of the phenylhydrazones to DHII and its derivatives occurs if the compound is redissolved in a suitable solvent, preferably an alcoholic solvent, e.g. ethanol or propanol and treated with an acid such as, for example, hydrochloric acid, acetic acid, or trifluoroacetic acid; heat may be required. Lewis acids, such as zinc chloride also catalyse the cyclisation reaction as do polyphosphonate esters in halogenated solvents such as chloroform. It is also observed that if phenylhydrazine salts are employed in the first step of this two step reaction sequence the intermediate phenylhydrazone derivative may not be isolated and in such instances the cyclised DHII product is formed directly. A similar result is obtained if the reaction between phenylhydrazines and indanones is carried out in acetic acid as solvent.

The product dihydroindenoindoles (DHII) are separated from the reaction mixtures by dilution with water, and either by filtration, or by solvent extraction. Further purification is achieved by crystallization from a suitable solvent, or by column chromatography using silica as the column material. In a further variant of the cyclisation reaction the phenylhydrazones may be heated with silica in the absence of a solvent. The product dihydroindenoindole may then be extracted from the silica at the end of the reaction with a suitable solvent; purification is achieved as before.

b. 5,6-Dihydroindeno[2,1-b]indole (iso DHII, IB) and analogues containing functional groups on the atoms of the benzenoid rings and disubstituents of C-5 may be prepared by the Fischer indole synthesis.

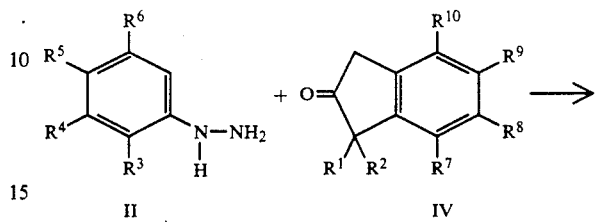

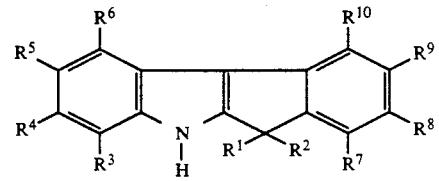

2-Indanone (IV) or an equivalent starting material, with appropriate functional group substitution in the benzenoid ring and at C-1 may be reacted with phenylhydrazines (II), or their salts. For compounds where $R^1$ and $R^2$ are hydrogen or $R^1$ is a lower alkyl and $R^2$ is hydrogen, $R^7$ to $R^{10}$ should be hydrogen. When $R^1$ and $R^2$ are lower alkyl then $R^3$, $R^4$, $R^5$, $R^6$, $R^7$, $R^8$, $R^9$ and $R^{10}$ have the meaning given under formula IB above. The reaction conditions and other reactants are similar to these described for DHII in process a. above.

c. An alternative to the synthesis of the DHII skeleton involves the cyclisation of the appropriate 3-benzoylindoles (V) and reduction of the tetracyclic ketones (VI) obtained.

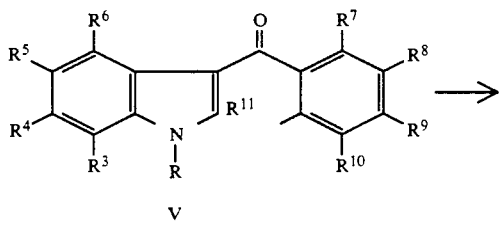

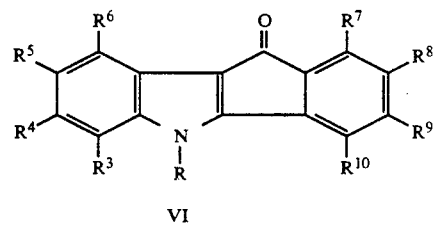

R, $R^1$, $R^2$, $R^3$, $R^4$, $R^5$, $R^6$, $R^7$, $R^8$, $R^9$ and $R^{10}$ have the meaning given under formula IA above. Here cyclisation is achieved by reaction of the ketone with palladium (O). $R^{11}$ is hydrogen when the cyclisation is performed with Pd. Compounds where the benzoyl group bears an iodo substituent ortho to the carbonyl group are better cyclised by exposure to ultraviolet light. $R^{11}$ is halogen, preferably iodine, bromine, when the cyclisation is performed by a photochemical reaction.(For references to the unsubstituted benzoyl compounds and their cyclisation see Synthesis, 607 (1978), and Heterocycles, 2433 (1983); reference to the photochemical cyclisation reaction is found in Chem. Soc. Perkin Trans. 1, 1523 (1974).

Reduction of the tetracyclic ketones can be achieved by reaction with such reagents as lithium aluminium hydride in diethyl ether, or tetrahydrofuran. Alternatively the carbonyl group may be reduced using Wolff-Kishner reduction.

d. An alternative synthesis of the 5,6-dihydroindeno[2,1-b]indole (iso-DHII) skeleton involves the reaction of an appropriate dianion VIII prepared by metallation, e.g. lithiation, of the corresponding ortho halo anilide VII, with a suitable alpha halo ketone, IX, according to the method of Wender and White (Tetrahedron 39,3767 (1983)),

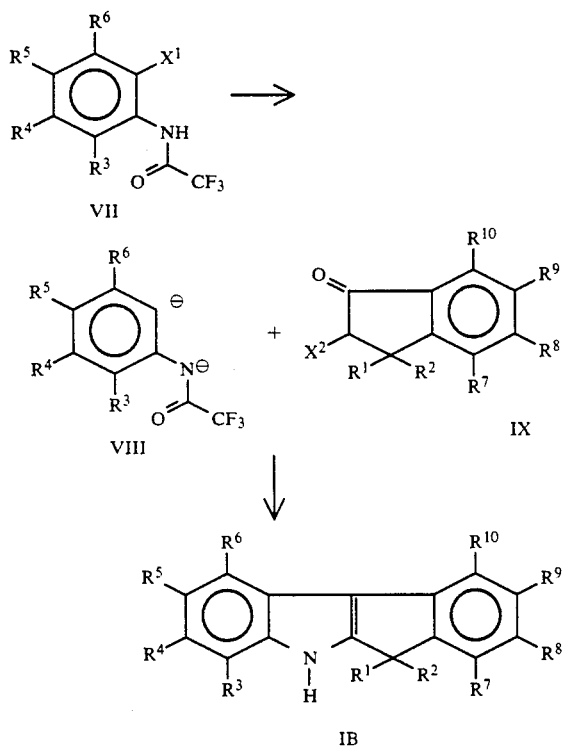

$R^1$, $R^2$, $R^3$, $R^4$, $R^5$, $R^6$, $R^7$, $R^8$, $R^9$ and $R^{10}$ have the meaning given under formula IB above.

$X^1$ is halogen, e.g. bromine, $X^2$ is chlorine, in some cases when the expected ring closure does not readily occur, a further treatment with strong base, e.g. potassium tert.butoxide, is needed to accomplish the reaction.

Modification of preformed DHII (IA) and iso-DHII (IB) compounds e. 5-alkyl DHII derivatives are synthesised by N-alkylation of corresponding 5H-DHII compounds dissolved in an aprotic solvent e.g. acetone, acetonitrile, dimethylsulfoxide (DMSO), dimethylformamide (DMF) with a base, such as sodium hydride, followed by an alkyl halide, or alkyl sulphate i.e. R-halide or R-sulphate, wherein R is a lower alkyl group.

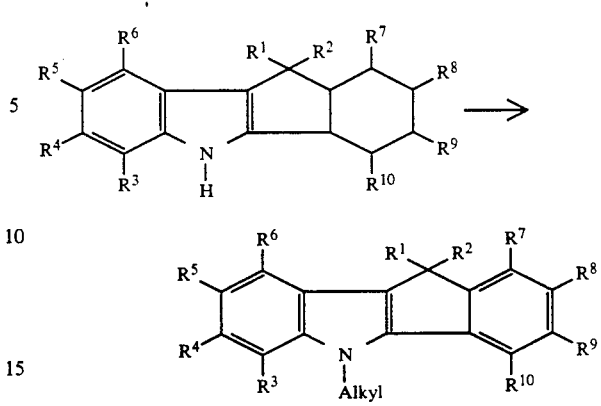

5-methyl compounds are preferably synthezised by using a solution of sodium hydride in dimethylsulfoxide followed by the addition of dimethylsulphate as alkylating reagent. 6-Alkyl iso DHII derivatives are synthesized in an analogous way as described above.

f. Hydroxy substituted compounds can be prepared from the corresponding alkoxy substituted ones by standard ether dealkylation methods, e.g. using different Lewis acids.

g. N-Alkylamino substituted compounds can be obtained from the corresponding N-acyl ones by conventional reduction procedures or via alkylation followed by reduction.

h. N-Acylamino substituted components can be obtained from the corresponding amines by conventional acylation procedures.

The following illustrates the principle and the adaption of the invention, however, without being limited thereto. Temperature is given in degrees Celsius.

WORKING EXAMPLES

EXAMPLE 1

5,10-Dihydroindeno[2-b]indole

A mixture of 1-indanone (13.21 g, 0.1 mol), and phenylhydrazine hydrochloride (14.48 g, 0.1 mmol), was heated in glacial acetic acid (150 cm$^3$). As the temperature of the solution approached reflux, the hydrazine hydrochloride dissolved. Soon after, a brown solid precipitated out of solution. The heat was immediately removed, and the reaction allowed to cool. The solid was filtered off, washed with copious amounts of water, and allowed to dry on a sinter. The solid was added to absolute ethanol (150 cm$^3$), heated to boiling, and filtered hot. The product was washed with cold ethanol (150 cm$^3$), and dried in a vacuum oven to yield a beige solid title compound. Yield: 18.50 g (90%). M.p. 258°-9° C. $^1$H NMR (DMSO-d$_6$) δ: 3.67. (2H, s,), 7.07 (1H, ddd,), 7.14 (1H, ddd,), 7.20 (1H, ddd,), 7.36 (1H, dd,), 7.51 (1H, d,), 7.52 (1H, d,), 7.57 (1H, d,), 7.67 (1H, d,), 11.6 (1H, br,).

EXAMPLE 2

5,10-Dihydro-5-methylindeno[1,2-b]indole

Sodium hydride (375 mq, 15.6 mmol) was added to dimethylsulfoxide (DMSO) (13 cm$^3$) under an atmosphere of nitrogen. The solution was then heated to 70° C. until no more gas (H$_2$) evolved. The solution was cooled to room temperature and 5,10-dihydroindeno[1,2-b]indole (2.69 g, 13.1 mmol) dissolved in a minimum amount of DMSO was added. After stirring at room temperature for 1 hour, dimethyl sulphate (1.5 cm³, 15 mmol) was introduced, and stirring continued for a further 1 hour. Water (3 cm³) was cautiously added, and the reaction then poured into ice/water. The solid thus formed was collected by suction filtration, washed firstly with water, dried on the water pump, and then washed with petrol (60°–80° C.). Crystallization from ethanol yielded colourless needles of the title compound. Yield: 1.52 g (53%). M.p. 152° C. ¹H NMR (CDCl³) δ: 3.55 (2H, s,), 3.85 (3H, s,), 6.8–7.4 (8H, m, arom.).

EXAMPLE 3

5,10-Dihydro-8-methoxyindeno1,2-b]-indole

To a stirred solution of p-methoxyphenylhydrazine hydrochloride (3.5 g, 20 mmol) and 1-indanone (2.35 g, 20 mmol) in absolute ethanol (80 cm³) was added dropwise triethylamine (2.01 cm³ 20 mmol). Stirring was continued until the thin liquid chromatography analysis of the reaction mixture indicated that no starting materials remained (about 1 hour). The solvent was removed, and the yellow residue was heated at reflux in a solution of polyphosphonate ester in chloroform (made by boiling phosphorus pentoxide (50 g) in chloroform (100 cm³) and diethyl ether (50 cm³) for 12 hours). After 1 hour, the solvent was removed, and the black residue stirred in water (200 cm³). This mixture was extracted 3 times with diethylether, the organic phases washed with water, and dried (MgSO₄). Removal of the solvent yielded a beige solid, which was crystallised from ethyl acetate/petrol (60°–80° C.) to give beige platelets of the title compound. M.p. 207° C., Yield: 3.8 g (78%). ¹H NMR (DMSO-d₆) δ: 3.66 (2H, s,), 3,79 (3H, s,), 7.4–7.6 (7H, m,), 11.4 (1H, br,).

EXAMPLE 4

5,10-Dihydro-10-methylindeno[1,2-b]indole

3-Methyl-1-indanone (500 mg, 3,42 mmol) prepared by an analogous method to that described by A. M. Weidler et al., Acta Chem. Scand., 18 p. 148 (1964) and phenylhydrazine (0.35 cm³, 3.5 mmol), were heated to reflux in glacial acetic acid (20 cm³). After 2 minutes concentrated hydrochloric acid (1 cm³) was added down the reflux condenser. Boiling was continued for 75 minutes and then the reaction was cooled. The solution was poured into ice/water and extracted into ethyl acetate. The extracts were washed consecutively with brine and then water, and dried (MgSO₄). Evaporation of solvent in vacuo, and column chromatography of the residue (10% EtOAc/petrol [60°–80° C.]) yielded the title compound as a cream solid. Yield: 320 mg (43%). M.p. 153°–155° C. ¹H NMR (DMSO-d₆) δ: 1.50 (3H, d,), 3.85 (1H, q.), 7.0–7.6 (8H, m.), 11.55 (1H, s,).

EXAMPLE 5

5,10-Dihydro-10,10-dimethylindeno[1,2-b]indole

A solution of 3,3-dimethyl-1-indanone (20,0 q, 0,125 mol) prepared by the method described by R. Knorr et al., Leibig's Annalen, 1207 (1980) and phenylhydrazine (12.3 cm³, 0.125 mol) in glacial acetic acid (200 cm³), was heated to reflux. Concentrated hydrochloric acid (10 cm³) was added via the condenser, and boiling continued for a further 2 hours. The solution was allowed to cool, and then poured into water (500 cm³). The water was extracted with diethylether three times, the combined extracts were washed with brine and water, and dried (MgSO₄). The solvent was removed, and petrol (60°–80° C.) added to the residue. The suspension was heated until boiling, The solid product was filtered off and the mother liquor concentrated. On cooling, more solid was obtained, and additional product separated out as the mother liquor was concentrated further. The solids were combined and crystallised from petrol to give the title compound. Yield: 10,2 g (35%). M.p. 160° C. ¹H NMR: (CDCl₃) δ: 1.60 (6H, s,), 7.1–7.7 (8H, m,), 8.16 (1H, s,).

EXAMPLE 6

5,10-Dihydro-6,8B-dimethylindeno[1,2-b]indole

A solution of 2,4-dimethylphenylhydrazine hydrochloride (1.27 g, 7.35 mmol), and 1-indanone (1 g, 1.1 eq), in glacial acetic acid (15 cm³), was heated to reflux for 30 minutes. The reaction mixture was cooled, and poured into ice/water (200 cm³). This solution was saturated with salt, and extracted into diethylether. The ethereal solution was dried (MgSO₄) and evaporated in vacuo. The excess acetic acid was removed by distillation with toluene and petroleum ether (60°–80° C.) in vacuo to leave a dark coloured solid. The product was purified first by "suction flash" chromatography, and then crystallization from petrol (60°–80° C.) to yield the title compound as a colourless solid. Yield: 0.53 g (31%). M.p. 182° C. ¹H NMR (CDCl₃) δ: 2.42, 2.46 (6H,s,), 3.62 (2H, s,), 6.7–7.6 (6H, m,), 8.05 (1H, br,).

EXAMPLE 7

5,6-Dihydroindeno2,1-b]indole

2-Indanone (5.25 g, 39.7 mmol) and phenylhydrazine hydrochloride (5.74 g, 39.7 mmol), were heated to reflux in glacial acetic acid (60 cm³) for 1 hour, and then cooled. The solution was poured into ice/water, and the solid precipitate collected by filtration. After partial purification by column chromatography, and crystallization (charcoal) from ethyl acetate to yielded colourless needles of the title compound. Yield 0.64 g (80%). M.p. 205° C. ¹H NMR (DMSO-d₆) δ: 3.65 (2H, s,), 7.0–7.2 (8H,), 10.40 (1H, br,).

EXAMPLE 8

5,10-Dihydro-6-chloroindeno[1,2-b]indole i) The o-chlorophenylhydrazone of 1-indanone (m.p. 128° C., 72 mg, 0.28 mmol) was absorbed onto silica (Merck No. 7736, 500 mg) from dichloromethane. The powder was heated to 140° C. under a water aspirated vacuum for 30 minutes. On cooling, the product was extracted from the silica with ethyl acetate and the solvent was then removed. The residue was purified by elution through a pad of "flash" silica with 5% ethyl acetate/petrol (60°–80° C.), to give a colourless solid title compound. Yield 47 mg (65%).

ii) The o-chlorophenylhydrazone of 1-indanone (650 mg, 2.5 mmol) was boiled in a chloroform solution of polyphosphonate ester (see the preparation of 5,10-dihydro-8-methoxyindeno[1,2-b]indole) for 30 minutes. The solvent was removed, and the residue stirred in water (75 cm³) for 1 hour. Extraction into diethylether gave a green solution which was washed with water, dried (MgSO₄), and evaporated. Purification by column chromatography (R$_f$ [5% EtOAc/petrol (60°–80° C.)]0.5), gave the title compound as a colourless solid. Yield 500 mg, (82%). M.p. 139° C. ¹H NMR (CDCl₃) δ: 3.72 (2H,s,), 7.0–7.6 (7H, m,), 8.5 (1H, br,).

EXAMPLE 9

5,10-Dihydro-8-methylindeno1.2]indole

A mixture of p-tolylhydrazine hydrochloride (9.75 g, 61.5 mmol) and 1-indanone (8.13 g, 61.5 mmol) was heated to reflux in ethanol (60 cm³) containing concentrated hydrochloric acid (5 cm³). After heating for two hours, the reaction mixture was allowed to cool slowly to room temperature. The product which separated out, was filtered off, washed with 10% aqueous ethanol, and dried in a vacuum oven, to yield the title compound as a colourless crystalline solid. Yield: 10.0 g, (74%). M.p. 225° C. (from ethanol). $^1$H NMR (DMSO-d$_6$)δ: 2.4 (3H,s,), 3.6 (2H, s,), 7.8–8.7 (7H, m,), 11.7 (1H, br,).

EXAMPLE 10

5,10-Dihydro-8-iso-propylindeno[1,2-b]indole

A mixture of 4-isopropylphenylhydrazine hydrochloride (6.3 g, 34 mmol) and 1-indanone (4.5 g, 34 mmol) were heated to reflux in ethanol (40 cm³) containing concentrated hydrochloric acid (2 cm³). Heating was continued for 4 hours, and then the reaction mixture was cooled to room temperature during which time the product crystallised out of solution as colourless crystals. This compound was filtered off, dried in a vacuum oven, and recrystallised from ethanol/water to yield colourless prisms. Yield: 6.59 g, (79%). M.p. 193° C. (from ethanol/water). $^1$H NMR (DMSO-d$_6$) δ: 1.27 (6H, d,), 2.96 (1H, septet,), 3.65 (2H, s,), 6.9–7.6 (7H, m,), 11.2 (1H, br,).

EXAMPLE 11

5,10-dihydro-2-methoxy-1,3-dimethylindeno[1,2-b]indole

A mixture of 5-methoxy-4,6-dimethyl-1-indanone (3.0 g, 16 mmol) and phenylhydrazine hydrochloride (2.3 g, 16 mmol) was heated to reflux in ethanol (20 cm³) containing concentrated hydrochloric acid (2 cm³). The reaction mixture was heated at reflux for 6 hours, and cooled to room temperature. Water was added, and the resulting precipitate filtered off. This product was dried in a vacuum oven, and purified by column chromatography to yield the title compound as a colourless solid. Yield: 2.8 g, (67%). M.p. 177° C. from ethyl acetate petrol (60°–80° C.). $^1$H NMR (CDCl$_3$)δ: 2.36 (6H, s,), 3.56 (2H, s,), 3.76 (3H, s,), 7.1–7.6 (5H, m,), 8.2 (1H,br,).

EXAMPLE 12

5,10-Dihydro-2-hydroxy-1,3-dimethylindeno[1,2-b]indole 5,10-Dihydro-2-methoxy-1,3-dimethylindeno[1,2-b]indole (2.4 g, 9.1 mmol) and pyridinium chloride (5.8 g) were mixed and heated to 200° C. for 30 minutes. The reaction mixture was cooled, and partitioned between ethyl acetate and water. The organic phase was washed three times with 2 M hydrochloric acid, and then three times with water, and then dried (MgSO$_4$). The solvent was removed in vacuo, and the residue purified by column chromatography to give the title compound as colourless prisms. Yield: 1.5 g (66%). M.p. 190° C. (from dichloromethane). $^1$H NMR (DMSO-d$_6$) δ: 2.25 (3H,s,), 2.26 (3H,s,), 3,50 (2H, s,), 6.9–7.5 (5H, m,), 8.16 (1H, br,), 11.33 (1H, br,).

EXAMPLE 13

5,10-Dihydro-2-methoxy-1.3-dimethyl-8-isopropylindeno[1,2-b]indole

A mixture of 5-methoxy-4,6-dimethyl-1-indanone (3.1 g, 16 mmol) and p-isopropylphenylhydrazine hydrochloride (3.05 g, 16 mmol), was heated to reflux in ethanol (20 cm³) containing concentrated hydrochloric acid (2 cm³). The reaction mixture was then heated at reflux for 4 hours and then allowed to cool to room temperature. The crystalline precipitate which formed, was filtered off, washed with 10% aqueous ethanol, and dried in a vacuum oven, to give the title compound as a pale green crystalline solid. Yield 3.04 g (62%). M.p. 130° C. (from ethanol). $^1$H NMR (CDCl$_3$) δ: 1.33 (6H, d,), 2.34 (3H, s,), 2.35 (3H, s,), 3.02 (1H, septet,), 3.6 (1H, br,), 3.76 (2H, s,), 7.08 (1H, s,), 7.30 (1H, d,), 7.45 (1H, s,), 8.12 (1H, s,).

EXAMPLE 14

5,10-Dihydro-8-tert.butylindeno1,2-b]indole

A solution of 4-tert.butylphenylhydrazine hydrochloride (1.74 g, 8.67 mmol) and 1-indanone (1.15 g, 1 eq) in ethanol (15 cm³) was heated to reflux. A couple of drops of concentrated hydrochloric acid was added, the reaction heated to reflux for 12 hours, and then cooled. The solid material was filtered to yield colourless needles, M.p. 202° C. $^1$H NMR (CDCl$_3$) δ: 8.15 (1H, br), 7.7–7.1 (7H, m), 3.7 (2H, br), 1.42 (9H, s).

EXAMPLE 15

5,10-Dihydro-2-hydroxy-1,3-dimethyl-8-isopropylindeno[1,2-b]indole 5,10-Dihydro-2-methoxy-1,3-dimethyl-8-isopropylindeno[1,2-b]indole (0.50 g, 1.64 mmol) was dissolved in dry dichloromethane (DCM, 2 cm³) under anhydrous conditions and cooled to −78° C. Boron tribromide (2 cm³ 1.2 eq of 1 M solution in DCM) was added, and warmed to room temperature, whereupon a suspension formed. After 20 minutes, this had re-dissolved. Water (2 cm³) was cautiously added, and the mixture extracted between more DCM, and saturated sodium bicarbonate solution (some solid around during extraction finally dissolved). The DCM layer was dried (Na$_2$SO$_4$) and filtered through a pad of "flash" silica, eluting with DCM to yield a white solid (0.43 g, 90%) M.p. 173° C.(dec.). $^1$H NMR (CDCl$_3$)δ: 8.04 (1H, br), 7.43 (1H, br), 7.29 (1H, d, J=8.2), 7.04 (1H, br), 4.58 (1H, br), 3.55 (2H, br), 30.2 (1H, septet, J=7.0Hz, 2.30 (3H, s), 2.29 (3H,s), 1.33 (6H, d, J=7.0Hz).

EXAMPLE 16

5,10-Dihydro-2-methoxy-1,3,6,8-tetramethylindeno[1,2-b]indole 4,6-Dimethyl-5-methoxy-1-indanone (2.2 g, 11.6 mmol) and 2,4-dimethylphenylhydrazine hydrochloride (2.00 g, 1 eq) were heated to reflux in ethanol (15 cm³) containing conc. HCl (1 cm³). After 2 hours, the precipitate was filtered and washed with ammonium hydroxide solution. All the collected material was extracted with ethyl acetate with the aid of salting out. The solvent was dried, and evaporated in vacuo and the product purified by column chromatography, eluting with 5% EtOAc/60°–80° petrol. The indole was recrystallised from dichloromethane/60°–80° petrol as pale beige needles. M.p. 210° C. $^1$H NMR (CDCl$_3$)δ: 8.03 (1H, br), 7.25 (1H, s), 7.15 (1H, s), 6.81 (1H, s), 3.76 (3H, s), 3.53 (2H, s), 2.49 (3H, s), 2.43 (3H, s), 2.37 (6H, s).

EXAMPLE 17

5,10-Dihydro-2,8-dimethoxy-1,3-dimethylindeno[1,2 b]indole

A solution of 4,6-dimethyl-5-methoxy-1-indanone (3.32 g, 17.5 mmol) and 4-methoxyphenylhydrazine hydrochloride (3.05 g, 1 eq) in ethanol (25 cm$^3$) containing hydrochloric acid (1 cm$^3$) was heated to reflux for 2 hours. The solvent was removed after cooling, and the material extracted between diethyl ether and sodium bicarbonate solution. The organic layer was dried, evaporated, and purified by column chromatography eluting with 50% dichloromethane-/60°-80° petrol to yield a pale yellow solid (2.30 g, 45%). M.p. 180° C. (from EtOAc/60°-80° petrol). $^1$H NMR (CDCl$_3$)δ: 8.10 (1H, br), 7.19 (1H, d, J=8.6Hz), 7.06 (1H, d, J =2.3Hz), 6.98 (1H, s), 6.79 (1H, dd, J=8.6, 2.3), 3.87 (3H, s), 3.75 (3H, s), 3.49 (2H, s), 2.33 (3H, s), 2.31 (3H, s).

EXAMPLE 18

5,10-Dihydro-8-fluoroindeno[1,2-b]indole

A mixture of 4-fluorophenylhydrazine hydrochloride (1.83 g, 11.25 mM) and 1-indanone (1.49 g) in ethanol (20 cm$^3$) was heated to reflux, and conc. hydrochloric acid was (1 cm$^3$) added. Heating was continued for 5 hours, and the reaction mixture was cooled. The product which crystallised out from the cold solution as coloured platelets, was collected by filtration and dried (1.90 g, 75%). M.p. 225°-227° C. (from ethyl acetate/petrol [60°-80 ]). $^1$H NMR (CDCl$_3$) δ: 8.3 (1H, br, s), 7.6-6.9 (7H, m), 3.70 (2H, s).

EXAMPLE 19

5,6-Dihydro-9-methoxyindeno2,1b]indole

4-Methoxyphenylhydrazine hydrochloride (3.5 g) and 2-indanone (2.6 g) were dissolved in ethanol (25 cm$^3$) containing conc. hydrochloric acid (0.5 cm$^3$) and the solution was heated at reflux for 2 hours. The solvent was then removed under reduced pressure to give a black residue which was treated with ethyl acetate and filtered. The filtrate was mixed with silica (25 g) and the solvent removed under reduced pressure, the residue was then placed at the top of a silica column and eluted with ethyl acetate: 60°-80° C. petroleum ether (1:10) to afford the indole (2.35 g, 50%) as pale brown needles. M.p. 170°-171° C. $^1$H NMR δ:3.65 (2H, s), 3.90 (3H, s), 6.84 (1H, dd, J=8.5 and 2.5Hz), 7.08 (1H, ddd, J=7.5, 7.5 and 1.0Hz), 7.20 (1H, d, J=8.5Hz), 7.24 (1H, ddd, J=7.5, 7.5 and 0.5Hz), 7.30 (1H, d, J=2.5Hz), 7.39 (1H, d, J=7.5Hz, 7.61 (1H, d, J=7.5Hz), 8.09 (1H, br.s).

EXAMPLE 20

5,6-Dihydro-9-isoproylindeno2,1-b]indole

A suspension of 4-isopropylphenylhydrazine hydrochloride (3.13 g, 16.8 mM) and 1-indanone (2.22 g, 1 eq.) was heated to reflux in absolute ethanol (20 cm$^3$) containing conc. hydrochloric acid (0.5 cm$^3$) for four hours. The ethanol was removed in vacuo, and the product partially purified by column chromatography, eluting with 10% ethyl acetate/petroleum ether (60°-80° C.) and finally purified by crystallization from ethyl acetate/petrol. This gave pale green needles (0.84 g, 18.7%). M.p. 144° C. $^1$H NMR δ:8.05 (1H, br.s), 7.7-7.0 (7H, m), 3.65 (2H, s), 3.07 (1H, septet, J=7.0Hz), 1.35 (6H, d, J=6.9Hz).

EXAMPLE 21

5,6-Dihydro-9-tertbutylindeno2,1-b]indole

2-Indanone (2.0 g, 15.2 mM) in ethanol (25 cm$^3$) containing 30% aqueous hydrochloric acid (0.5 cm$^3$) was stirred and heated with 4-tert.butylphenylhydrazine hydrochloride (3.0 g, 15.2 mM) for 4 h. Silica gel (3.0 g) was then added and the solvents removed under reduced pressure. The residue was then added to the top of a column of silica (28 g) and eluted with 5% ethyl acetate in 60°-80° C. petrol. Repeated chromatography gave the expected product (0.35 g, 9%), M p. 182° C. $^1$H NMR δ: 1.44 (9H, s), 3.71 (2H, s), 7.10 (1H, ddd, J=7.5, 7.5, 1.5Hz), 7.22-7.42 (4H, m), 7.68 (1H, br.d, J=7.0Hz),7.84 (1H, br.s), 8.15 (1H, s).

EXAMPLE 22

2-(N-Acetylamino-5,10-dihydroindeno[1,2-b]indole

A solution of phenylhydrazine (4.05 g, 37.5 mM), 5-(N-acetylamino)indan-1-one (Prepared by the method of N. L. Allinger and E. S. Jones (J. Org. Chem., 1962, 27, 70) (5.8 g, 30.7 mM), and 4-toluenesulphonic acid (0.005 g) in toluene (125 cm$^3$) was heated in a Dean Stark apparatus for 2 hours. The reaction mixture was cooled and the product hydrazone filtered off as a pale brown microcrystalline solid (7.3 g, 85%), M.p. 252°-253° C. Finely crushed hydrazone (8.5 g, 30 mM) from the above experiment was added with stirring to a solution of polyphosphoric ester, prepared from phosphorus pentoxide (30 g), chloroform (30 cm$^3$), and diethyl ether (cm$^3$) together for 24 hours. Excess solvents were evaporated off and the residue heated at 60° C. for 45 min. After cooling, the tarry residue was poured into water (150 cm$^3$) and chloroform (40 cm$^3$) and the mixture was agitated vigorously for 10 min. The dark coloured solid which remained was collected and mixed with silica (6 g), and then added to the top of a column of silica (20 g) and the column was eluted with ethyl acetate. A pale yellow solid product was obtained from the eluant. Yield: 2.0 g, 27%. M.p. >240° C. $^1$H NMR (CDCl$_3$) δ: 2.11 (3H, s), 3.50 (2H, s), 6.95-7.10 (2H, m), 7.33-7.50 (4H, m), 7.67 (1H, br.s).

EXAMPLE 23

5,10-Dihydro-2-(N-ethylamino)indeno[1,2-b]indole

A solution of 5,10-dihydro-2-(N-acetylamino)indeno[1,2,b]-indole (0.70 g, 2.8 mM) in dry tetrahydrofuran (50 cm$^3$), under a protective atmosphere of nitrogen, was treated with lithium aluminium hydride (0.40 g, 10.50 mM) during the course of 3 hours. The mixture was then heated to reflux for a further 3 hours, and eventually cooled. Excess reagent was destroyed by the addition of a saturated solution of sodium potassium tartrate (5 cm$^3$) and the organic phase separated. The residual aqueous slurry was extracted with tetrahydrofuran (3×10 cm$^3$) and the extracts and organic phase were combined, filtered through phase transfer paper, and evaporated. This gave the title compound as a pale yellow solid. M.p. 225° C. Yield; 0.47 g, 71%. $^1$H NMR (CDCl$_3$) δ: 1.23 (3H, t, J=7.0 Hz), 3.09 (2H, q, J=7.0Hz), 3.59 (2H, s), 4.80 (1H, br.s), 6.56 (1H, d, J=7.5Hz), 6.87 (1H, s), 7.01 (2H, br.m), 7.32-7.48 (3H, br.m), 10.47 (1H, br.s).

EXAMPLE 24

5,10-Dihydro-2-(N-acetyl-N-ethylamino)indeno[1,2-b]indole 5,10-Dihydro-2-(N-Ethylamino)indeno[1,2-b]indole (0.47 g, 1,90 mM) and acetic anhydride (4 cm$^3$) were heated to 90°-95° C. for 4 hours. Water (30 cm$^3$) was added to the cold solution and the mixture was stirred vigorously for 1 hour. The solid product which formed was then collected and washed with a few drops of cold ethanol to afford the title compound 0.5 g, 90% as a colourless solid, M.p. 232° C. $^1$H NMR (CDCl$_3$) δ: 1.16 (3H, t, J=7.0 Hz), 1.90 (3H, s), 3.73 (2H, s), 3.81 (2H, q, J=7.0 Hz), 7.05-7.20 (4H, m), 7.46 (1H, d, J=7.5 Hz), 7.57 (1H, d, J=8.0 Hz), 7.63 (1H, d, J=7.0 Hz, 10.36 (1H, s)).

EXAMPLE 25

5,10-Dihydro-2-(N,N-diethylamino)indeno[1,2-b]indole 5,10-Dihydro-2-(N-Acetyl-N-ethylamino)indeno[1,2-b]indole (0.5 g, 1.7 mM) in dry tetrahydrofuran (80 cm$^3$), protected under an atmosphere of nitrogen, was treated with lithium aluminum hydride (0.3 g) during 1 hour. The reaction mixture was then heated to 50° C. for a further 1 hour, cooled, and saturated sodium potassium tartrate (5 cm$^3$) added. The solvent layer was decanted from the aqueous residue, and the latter washed with tetrahydrofuran (3×8 cm$^3$). The combined organic phase and washing were filtered through phase transfer paper and evaporated to yield a yellow solid. This was crystallised from 95% ethanol to afford the title compound 0.35 g as pale yellow prisms, M.p. 204°-206° C. After column chromatography (silica: ethyl acetate/60°-80° petrol), the M.p. of the compound was raised to 205°-206° C. (0.26 g, 55%).

EXAMPLE 26

5,10-Dihydro-6-methyl-8-methoxyindeno[1,2-b]indole i) 2-Methyl-4-methoxyphenylhydrazine hydrochloride (23.6 g, 0.125 mol) was added to a solution of sodium acetate (30.8 g, 0.375 mol) in 650 ml of water. The mixture was stirred until all the material was dissolved. Remaining coloured insoluble material was removed by filtration. To the resulting clear solution 1-indanone (13.2 g, 0.1 mol) dissolved in 150 ml of ethanol was added. The mixture was heated for 15 minutes on a water bath and then allowed to cool to room temperature. After stirring for 30 minutes at ambient temperature followed by cooling in an ice bath, the crystals formed were separated by filtration and washed with cold water. Recrystallization from ethanol gave 14.0 g (53%) of the 2-methyl-4-methoxyphenylhydrazone of 1-indanone. M.p. 131° C.

ii) A mixture of 14.0 g (0.053 mol) of the 2-methyl-4-methoxyphenylhydrazone of 1-indanone in 300 ml of ethanol was heated to 60° C., when most of the solid material had dissolved. 120 ml of HCl-saturated ethanol Was then added, and the resulting solution was then stirred for 15 minutes at room temperature. The solvent was removed by evaporation and the residue was then dissolved in methylene chloride and washed 3 times with 1 M sodium hydroxide solution and once with saturated sodium chloride solution. Drying (MgSO$_4$) and evaporation gave 13.2 g of crude product. This material was purified by chromatography on silica gel using methylene chloride as eluant giving 8.98 g (68%) of the expected compound. Recrystallization from hexane/ethyl acetate (9/1) gave 7.2 g of pure compound with m.p. 181° C. $^1$H-NMR (CDCl$_3$): 2,49 (3H, s), 3.67 (2H, s), 3.88 (3H, s), 6.68 (1H, s), 6.95 (1H, d), 7.16-7.25 (1H, dd), 7.3 (1H, t), 7.45 (1H, d), 7.5 (1H, d), 8.12 (1H, s).

EXAMPLE 27

5,10-Dihydro-8-methoxy-7,9-dimethylindeno[1,2-]indole

A mixture of 3,17 g (0.024 mol) of 1-indanone, 5.46 g (0.0269 mol) of 3,5-dimethyl-4-methoxyphenylhydrazine hydrochloride, 50 ml of acetic acid and 2.5 ml of conc. hydrochloric acid was refluxed for 1 hour. The reaction mixture was poured into an excess of aqueous sodium hydoxide solution, and the resulting mixture was then extracted with ether. Drying (MgSO$_4$) and evaporation afforded the crude product. Purification by combined recrystallization and column chromatography gave 1.47 g (23%) of the product. $^1$H NMR (CDCl$_3$): 2.42 (3H, s), 2.61 (3H, s), 3.28 (3H, s), 3.85 (2H, s), 7.07 ($^1$H, s), 7.19 ($^1$H, dd), 7.32 (1H, dd), 7.43 (1H, d), 7.53 (1H, d), 8.1 (1H, s).

EXAMPLE 28

5,10-Dihydro-8-hydroxy-7,9-dimethylindeno[1,2-b]indole

This compound was obtained in a small amount in the synthesis of Example 27, but could also be obtained by demethylation of 5,10-dihydro-8-methoxy-7,9-dimethylindeno[1,2-b]indole obtained in Example 27 analogous to Example 12. $^1$H NMR (CDCl$_3$): 2.39 (3H, s), 2.57 (3H, s), 3.84 (2H, s), 4.37 (1H, s), 7.05 (1H, s), 7.19 (1H, dd), 7.32 (1H, dd), 7.44 (1H, d), 7.53 ($^1$H, d), 8.04 (1H, s).

EXAMPLE 29

5,10-Dihydro-6-isopropylindeno[1,2-b]indole

A mixture of 12.6 g (0.096 mol) of 1-indanone, 19.7 g (0.105 mol) of 2-isopropylphenylhydrazine hydrochloride, 150 ml of ethanol and 10 ml of conc. hydrochloric acid was refluxed for 2 hours. The solvent was removed by evaporation and the residue suspended in acidic water. Extraction with ether, drying (MgSO$_4$) and evaporation gave the crude product, which was purified by column chromatography on silica gel using methylene chloride/light petroleum (2/8) as the eluant. The final purification was achieved by recrystallization from ethylacetate/light petroleum giving 14.0 g (59%) of the product. $^1$H NMR (CDCl$_3$) 1.48 (6H, d), 3.37 (1H, septet), 3.77 (2H, s), 4.37 (1H, s), 7.1-7.3 (3H, m), 7.37 ($^1$H, dd), 7.5-7.6 (3H, m), 8.03 (1H, s).

EXAMPLE 30

5,6-Dihydro-3-methoxy-2,4-dimethylindeno 2.1-b]indole i) Sulphonyl chloride (ca. 1 eq) was added dropwise over 30 minutes to a solution of 5-methoxy-4,6-dimethylindan-1-one (0.65 g, 3.4 mmol) in dry ether (10 cm$^3$), with stirring and in absence of light at 0° C. After the addition was complete, the reaction was allowed to warm up to room temperature, and stirring continued for a further 2 hours. The solvents were removed and the solid residue chromatographed, eluting with 50% dichloromethane/ -petroleum ether (60°-80° C.) and then with dichloromethane, to yield the dichloro derivative [R$_F$(DCM) 0.85, 0.14g, 14%] which was discarded, and the required 2-chloro-5-methoxy-4,6-dimethylindan-1-one [R$_F$(DCM) 0.7]. The latter is a colourless solid (0.65 g, 85%) m.p. 109°–110° C. $^1$H NMR (CDCl$_3$) δ: 7.53 (1H, s), 4.54 ($^1$H, dd, J=7.8, 3.7Hz), 3.79 (3H, s), 3.64 (1H, dd, J=17,5, 7.8Hz), 3.13 (1H, dd, J=17.5, 3.5HZ), 2.33 (3H, s), 2.25 (3H, s).

ii) A solution of o-bromotrifluoroacetanilide (325 mg, 1.2 mM) in tetrahydrofuran (THF)(20 cm$^3$) was cooled to −78° C. and to this was added methyl lithium (1 molar equivalent of a 1.4 M solution in diethyl ether). This addition was followed 10 minutes later by the introduction of tert-butyllithium (2 molar equivalent of a 1.7 M solution in pentane). The reaction mixture was stirred for 1 hour at −78° C., and then a solution of the chloroindanone (272 mg. 1.2 mM) in THF (3 cm$^3$) added dropwise via a cannula. The solution was allowed to warm slowly to room temperature, and stirred for one hour, then a 10% solution potassium hydroxide in methanol (3 cm$^3$) was introduced. After stirring for 30 minutes, the reaction mixture was poured into 2 M HCl, and extracted with dichloromethane (3 ×10 cm$^3$). The combined organic extracts were dried (Na$_2$SO$_4$) and evaporated in vacuo to afford a solid residue which was chromatographed on silica, eluting with 10% ethyl acetate/petroleum ether (60°–80° C.) to yield trifluoroacetanilide (R$_F$ 0.4)(50 mg), and the 2-chloro-1-hydroxy-5-methoxy-4,6-dimethyl-1-(2′-trifluoroacetamidophenyl)indane (R$_F$0.3) (220 mg, 44%). The latter compound is a colourless solid. M.p. 182° C. $^1$H NMR (CDCl$_3$)δ: 10.7 (1H, br), 8.25 (1H, dd), 7.36 (1H, ddd), 7.06 (1H, s), 6.98 (1H, ddd), 6.39 (1H, dd), 4.76 (1H, dd, J=4.8, 2.7Hz), 3.78 (3H, s), 3.63 (1H, s, exchanges with D$_2$O), 3.11 (2H, 2 ×2nd order multiplets), 2.33 (3H, s), 2.23 (3H, s).

iii) The chlorohydroxyindane (19 mg, 50 μmol) in THF (0.5 cm$^3$) was added dropwise to a solution of potassium tert-butoxide (2 molar equivalents) in dry 2-methylpropan2-ol (0.5 cm$^3$). The reaction mixture was stirred for 16 hours, whereupon water (0.25 cm$^3$) was added, and the organic solvents removed in vacuo. The residue was extracted between brine and dichloromethane, the organic extract dried (Na$_2$SO$_4$) and concentrated to about 1 cm$^3$ in vacuo. Methanolic potassium hydroxide (0.25 cm$^3$ of 10% solution) was added to the reaction, followed ten minutes later by trifluoroacetic acid (0.5 cm$^3$). After a further 30 minutes, the reaction was poured into a saturated solution of sodium bicarbonate, and the organic material extracted into dichloromethane. The solvent was removed in vacuo and the residue chromatographed on silica eluting with dichloromethane to yield the isoindenoindole as a colourless solid (9 mg, 70%). M.p. 179°–182° C. (dec). $^1$H NMR (CDCl$_3$)δ: 8.2, (1H, br), 7.82 (1H, m), 7.4–7.1 (4H, m), 3.74 (3H, s), 3.58 (2H, s), 2.4 (3H, s), 2.3 (3H, s).

EXAMPLE 31

5,6-Dihydro-3-hydroxy-2,4-dimethylindeno 2.1-b]indole

The 5,6-dihydro-2,4-dimethyl-3-methoxyindeno[2,1-b]indole (50 mg) in dichloromethane (1 cm$^3$) was cooled to −78° C. and treated with boron tribromide (0.1 cm$^3$). After stirring for a few minutes the reaction mixture was allowed to warm to room temperature and poured onto crushed ice. After the addition of excess sodium hydrogen carbonate the product was extracted from the reaction mixture with dichloromethane and the combined dried extracts were evaporated to give a colourless solid. Yield: 40 mg. This was chromatographed on silica eluting with dichloromethane to afford the title compound as a microcrystalline solid. M.p. 192°–194° C. $^1$H NMR δ$_H$:10.2(1H, br.s), 7.5–7.0 (5H, br.m), 3.62(2H,3), 2.35(3H,s), 2.30(3H,s).

Pharmacological Properties

The indenoindoles described in the present invention are hydrophobic structures which form cations, cation radicals or radicals upon oxidation. They constitute potent antioxidants as measured by inhibition of $Fe^{2+}$-ascorbate induced lipid peroxidation in vitro. The compounds of formulas (IA) and (IB) prevent efficient oxidation of lipoproteins in human plasma in the presence of rabbit smooth muscle cells or mouse peritoneal macrophages. They also prevent ischemic/reperfusion damage to the isolated perfused rat heart, and protect against carbon tetrachloride-, acetaminophen-, methylmethane sulfonate-, menadione-, t-butyl hydroperoxide-, and N-methyl-$N^1$-nitro-N-nitrosoguanidine-induced liver damage in mice, or in isolated rat hepatocytes.

These properties suggest that the structures of formulas (IA) and (IB) have a potential use in the protection or treatment of ischemic or reperfusion injury, particularly cerebral and cardiac ischemia/infarct, thrombosis and embolism, atherosclerosis, Parkinson's disease, Alzheimer's disease, ageing, neoplasms and toxicity of antineoplastic drugs and immuno suppressive agents, and inflammation including allergic/inflammatory conditions like Bronchial asthma and rheumatoid arthritis. Other potential applications are chemoprevention against chemical toxicity or radiation damage. The indenoindole compounds are not appreciably activated by UV light making them candidates for use in skin care products. Another interesting and important feature of the indenoindole compounds is their ability to stabilize membranes.

Pharmacological Tests

The most important feature of the compounds of the invention is their efficacy as free-radical scavengers or antioxidants. An assay system measuring the concentration of the compounds of formulas (IA) and (IB) required to inhibit lipid peroxidation by 50% (IC$_{50}$) was used. The lipid peroxidation assay is described below and the data presented in Table 1. Other assays described below are the red blood cell fragility test used for measuring membrane stabilisation by indenoindoles. (Table 2), and protection by indenoindoles against cytotoxicity of N-methyl-N′-nitro-N-nitrosoguanidine (MNNG) in rat hepatocytes (Table 3). MNNG is a highly cytotoxic agent, the mechanism of action of which may involve a radical-mediated membrane destabilization.

1. Ascorbate/$Fe^{2+}$-dependent lipid peroxidation

For the ferrous/ascorbate lipid peroxidation system, 6.25 ml of 0.1 M potassium phosphate buffer (KP$_i$), pH 7.4, was added to 12.5 mg dried soy bean phospholipids. After flushing with argon for 2 min, the suspension was sealed with five layers of Parafilm and sonicated until the suspension was translucent. The final reaction mixture was composed of 200 μg/ml phospholipid, 10 μM FeNH$_4$(SO$_4$)$_2$ or Fe(NH$_4$)$_2$(SO$_4$)$_2$, and 100 μM ascorbic acid in 0.1 M KP$_i$ (pH 7.4), and the antioxidant to be tested in acetone or DMSO. The volume of vehicle never exceeded 1% of the total volume. The reaction was initiated by the addition of ascorbic acid plus iron. The reaction was continued at room temperature in a shaking water bath for 30 min and then stopped by the addition of 10 μM of 0.5 M butylated hydroxytoluene in DMSO. The above procedure and the subsequent determination of 2-thibarbituric acid-reactive material is described in: Shertzer, H. G. et al, Biochem. Pharmacol. 37, 333 (1988). Table 1 shows the effects of indenoindoles and α-tocopherol on ascorbate/$Fe^{2+}$-dependent lipid peroxidation.

TABLE 1

| Compound | $pIC_{50}$ |
|---|---|
| 2-Ethylamino-DHII | 7.9 |
| 2-Diethylamino-DHII | 7.4 |
| 9-Methoxy-iso-DHII | 6.4 |
| 8-Methoxy-DHII | 6.2 |
| 6,8-Dimethyl-DHII | 6.1 |
| 10,10-Dimethyl-DHII | 6.1 |
| DHII | 5.8 |
| iso-DHII | 5.8 |
| 8-Methyl-DHII | 5.7 |
| 10-Methyl-DHII | 5.7 |
| 8-Isopropyl-DHII | 5.6 |
| 8-Fluoro-DHII | 5.6 |
| 6-Chloro-DHII | 5.2 |
| 5-Methyl-DHII | 5.1 |
| α-Tocopherol (Vitamin E) | 5.0 |

2. Membrane stabilization in red blood cells

The membrane stabilization effect of indenoindoles was assayed by the red blood cell fragility test. Rats were anesthetized with 65 mg phenobarbital per kg body weight by i.p. injection. Blood samples were removed into a heparinized syringe from the left ventricle and diluted 20-fold with buffer containing 140 mM NaCl, 10 mM sodium citrate and 5 mM glucose (pH 7.4) at 0° C. Diluted blood was kept on ice. A 0.75 ml aliquot of blood was added to a 4 ml cuvette containing 10 μl of the antioxidant dissolved in DMSO vehicle. After 1 min of gentle swirling, 0.75 ml of 0.9 NaCl or $H_2O$ were added to the cuvette by forceful pipetting, and the absorbance at 656 nm was recorded with a Beckman DU-70 spectrophotometer. When $H_2O$ was added in the absence of a stabilizing agent, absorbance decreased within 15 sec to 0.8. Addition of NaCl instead of $H_2O$ gave a time-independent absorbance of 2.2. In the presence of increasing concentrations of stabilizing chemicals, the absorbance decrease observed after the addition of water was diminished. The % protection from osmolysis was obtained from the equation $[[(2.2-0.8)-A]/(2.2-0.8)] \times 100\%$, where A=2.2 minus the absorbance decrease when water is added in the presence of a known concentration of chemical. The % protection is then plotted against several concentrations of the chemical being treated. The red blood cell fragility protective index value (RBC-PIV) is the linear regression slope of this plot, expressed as the percentage protection against osmolysis per μM protecting agent. Table 2 shows the RBC-PIV values for different indenoindoles and α-tocopherol.

TABLE 2

| Compound | RBC-PIV (%/μM) |
|---|---|
| 10,10-Dimethyl-DHII | 0.48 |
| DHII | 0.49 |
| iso-DHII | 0.50 |
| 5-methyl-DHII | 0.74 |
| α-tocopherol | 0.10 |

3. Protection against cytotoxic effects of MNNG in hepatocytes

The protective effects of indenoindoles on MNNG-induced cytotoxicity was assayed with rat hepatocytes. Hepatocytes were prepared from male Sprague-Dawley rats by collagenase treatment as originally described by Zahlten and Stratman (Zahlten, R. N. and Stratman, F. W., Arch. Biochem. Biophys. 163, 600 (1988)), as modified by Reitman et al. (Reitman, F. A. Shertzer, H. G. and Berger, M. L., Biochem. Pharmacol. 37, 3183 (1988)). In order to improve viability, cells were centrifuged through 0.508g/ml Percoll (Pharmacia AB, Uppsala, Sweden) in 137 mM NaCl, 8.1 mM $Na_2HPO_4$ and 1.5 mM $KH_2PO_4$(pH 7.4). Putative protecting agents were added to the cells as solutions in DMSO, with the final concentration of DMSO never exceeding 5 μl/ml of cell suspension. MNNG was added to a concentration of 0.5 mM as a solution in ethanol, giving a final concentration of ethanol of 1%; ethanol alone was by itself without effect. Viability was determined as the percentage of cells that excluded 0.2% trypan blue. The protective effects by indenoindoles and α-tocopheryl acetate on cytotoxicity are shown in Table 3. Values are the concentration of compound required to extend by 1 hour, the time needed for MNNG to kill 50% of the viable cells.

TABLE 3

| Compound | $IC_{50}$ (μM) |
|---|---|
| DHII | 3.1 |
| iso-DHII | 3.4 |
| 5-methyl-DHII | 6.0 |
| α-tocopheryl-acetate | 161 |

We claim:
1. A compound of the formula IA or IB

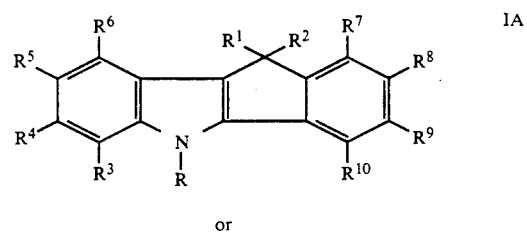

or

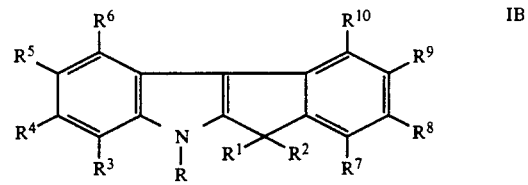

or a pharmaceutically acceptable salt thereof wherein R is hydrogen or an alkyl group containing 1-6 carbon atoms,
$R^1$ and $R^2$ are independently selected from hydrogen or an alkyl group containing 1-6 carbon atoms,
$R^3$, $R^4$ and $R^6$ are independently selected from hydrogen, halogen or an alkyl group containing 1-6 carbon atoms,
$R^5$ is hydrogen, hydroxy, halogen, an alkyl group containing 1-6 carbon atoms, an alkoxy group containing 1-6 carbon atoms, a mono- or dialkylamino group containing 1-4 carbon atoms in each alkyl part, NH₂ or

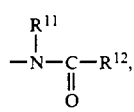

R⁷, R⁹ and R¹⁰ are independently selected from hydrogen, hydroxy, an alkyl group containing 1-6 carbon atoms, an alkoxy group containing 1-6 carbon atoms, a mono- or di-alkylamino group containing 1-4 carbon atoms in each alkyl part, NH₂ or

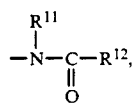

R⁸ is a mono- or dialkylamino group containing 1-4 carbon atoms in each alkyl part of

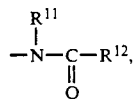

R¹¹ is hydrogen or an alkyl group containing 1-6 carbon atoms, and

R¹² is an alkyl group containing 1-6 carbon atoms.

2. A compound according to claim 1 wherein R⁸ is a mono- or dialkylamino group.

3. A compound according to claim 1 wherein R⁸ is

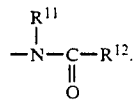

4. A compound according to claim 1 wherein at least one of R³ and R⁵ is an alkyl group containing 1-6 carbon atoms.

5. A compound according to claim 1 wherein R⁵ is an alkoxy group containing 1-6 carbon atoms.

6. A compound according to claim 1 wherein R, R⁴, R⁶, R⁷, R⁹ and R¹⁰ are hydrogen.

7. A compound according to claim 2 wherein R⁸ is ethyl- or diethylamino.

8. A compound according to claim 2 which is 5,10-dihydro-2-ethylaminoindeno[1,2-b]indole, or 5,10-dihydro-2-diethylaminoindeno[1,2-b]indole.

9. A compound according to claim 3 wherein R⁸ is NH-acetyl.

10. A compound according to claim 4 wherein at least one of R³ and R⁵ is methyl.

11. A compound according to claim 5 wherein R⁵ is methoxy.

12. The compound which is 5,10-dihydro-1,3,7,9-tetramethyl-2,8-dihydroxyindeno[1,2-b]indole or a pharmaceutically acceptable salt thereof.

13. The compound which is 5,10-dihydro-8,10-dimethyl9-methoxyindeno[2,1-b]indole or a pharmaceutically acceptable salt thereof.

14. The compound which is 5,10-dihydro-7-methyl-9-methoxyindeno[2,1-b]indole or a pharmaceutically acceptable salt thereof.

15. A method for treating a medical disorder associated with free radical formation which comprises administering to a patient in need of such treatment an effective amount of a compound of the formula IA or IB

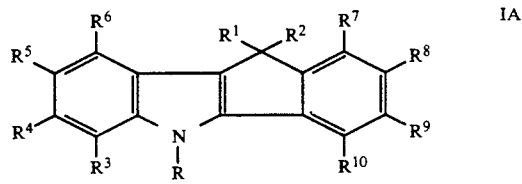

or

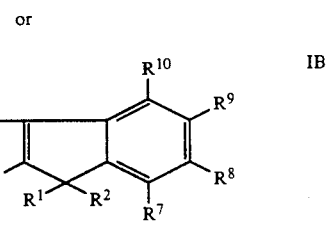

or a pharmaceutically acceptable salt thereof,
wherein R is hydrogen or an alkyl group containing 1-6 carbon atoms,
R¹ and R² are independently selected from hydrogen or an alkyl group containing 1-6 carbon atoms,
R³, R⁴ and R⁶ are independently selected from hydrogen, halogen or an alkyl group containing 1-6 carbon atoms,
R⁵ is hydrogen, hydroxy, halogen, an alkyl group containing 1-6 carbon atoms, an alkoxy group containing 1-6 carbon atoms, a mono- or di-alkylamino group containing 1-4 carbon atoms in each alkyl part, NH₂ or

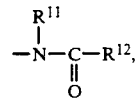

R⁷, R⁹ and R¹⁰ are independently selected from hydrogen, hydroxy, an alkyl group containing 1-6 carbon atoms, an alkoxy group containing 1-6 carbon atoms, a mono- or di-alkylamino group containing 1-4 carbon atoms in each alkyl part, NH₂ or

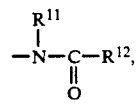

R⁸ is a mono- or dialkylamino group containing 1-4 carbon atoms in each alkyl part of

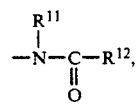

$R^{11}$ is hydrogen or an alkyl group containing 1-6 carbon atoms, and $R^{12}$ is an alkyl group containing 1-6 carbon atoms.

16. A method for treating a medical disorder associated with free radical formation which comprises administering to a patient in need of such treatment an effective amount of a compound selected from the group consisting of 5,10-dihydro-1,3,7,9-tetramethyl-2,8-dihydroxyindeno[1,2-b]indole; 5,10-dihydro-8,10-dimethyl9-methoxyindeno[1,2-b]indole; or 5,10-dihydro-7-methyl-9-methoxyindeno[2,1-b]indole or a pharmaceutically acceptable salt thereof.

17. A method according to claim 15 or 16 wherein the disorder is ischemic or reperfusion injuries, thrombosis or embolism.

18. A method according to claim 15 or 16 wherein the disorder is a neoplasm.

19. A method according to claim 15 or 16 wherein the disorder is Parkinson's disease, Alzheimer's disease or ageing.

20. A method according to claim 15 or 16 wherein the disorder is atherosclerosis.

21. A method according to claim 15 or 16 wherein the disorder is an allergic/inflammatory condition such as bronchial asthma or rheumatoid arthritis.

22. A method according to claim 15 or 16 wherein the disorder is due to damage caused by chemicals, radiation, or antineoplastic or immunosuppressive agents.

23. A pharmaceutical composition comprising an active ingredient which is a compound as defined in claim 1, 12, 13 or 14 or a pharmaceutically acceptable salt thereof in a pharmaceutical acceptable carrier.

* * * * *

UNITED STATES PATENT AND TRADEMARK OFFICE
CERTIFICATE OF CORRECTION

PATENT NO. : 5,185,360

DATED : February 9, 1993

INVENTOR(S) : Sainsbury et al.

It is certified that error appears in the above-identified patent and that said Letters Patent is hereby corrected as shown below:

col. 1, line 7, insert --The invention described herein was made with government support and the government has certain rights in the invention.--;

col. 5, line 8, delete "$\begin{array}{c} R^{11} \\ | \\ -N-C-R^{12} \\ \| \\ O \end{array}$";

col. 5, line 17, after "or" insert --$\begin{array}{c} R^{11} \\ | \\ -N-C-R^{12} \\ \| \\ O \end{array}$--;

col. 6, line 20, "$NHCRO^{14}$" should read --$NHCOR^{14}$--;

col. 6, line 54, "aoetamidoindeno" should read --acetamidoindeno--;

col. 13, line 59, "20,0q" should read --20,0g--;

col. 14, line 13, after "8" delete "B";

col. 14, line 32, "2,1-b]" should read --[2,1-b]--;

col. 15, line 3, "1.2]" should read --[1,2]--;

UNITED STATES PATENT AND TRADEMARK OFFICE
CERTIFICATE OF CORRECTION

PATENT NO. : 5,185,360

DATED : February 9, 1993

INVENTOR(S) : Sainsbury et al.

It is certified that error appears in the above-identified patent and that said Letters Patent is hereby corrected as shown below:

col. 16, line 3, "1.3" should read --1,3--;

col. 16, line 22, "1,2-b]" should read --[1,2-b]--;

col. 17, line 57, "isoproylindeno2" should read --isopropylindeno[2--;

col. 18, line 5, "2,1-b]" should read --[2,1-b]--;

col. 18, line 52, "[1,2,b]" should read --[1,2-b]-- col. 20, line 8, "[1,2-]" should read --[1,2-b]--;

col. 20, line 21, "($^1$H,s)" should read --(1H,s)--;

col. 20, line 21, "($^1$H,dd)" should read --(1H,dd)--;

col. 20, line 34, "($^1$H,d)" should read --(1H,d)--;

col. 20, line 53, "($^1$H,dd)" should read --(1H,dd)--;

col. 20, line 56, "2.1-b]" should read --[2,1-b]--;

col. 21, line 4, "($^1$H,dd," should read --(1H,dd,--;

col. 21, line 58, "2.1-b]" should read --[2,1-b]--;

col. 25, line 24, "of" should read --or--;

UNITED STATES PATENT AND TRADEMARK OFFICE
CERTIFICATE OF CORRECTION

PATENT NO. : 5,185,360
DATED : February 9, 1993
INVENTOR(S) : Sainsbury et al.

It is certified that error appears in the above-identified patent and that said Letters Patent is hereby corrected as shown below:

col. 25, line 66, "5,10" should read --5,6--;

col. 25, line 67, "thyl9" should read --thyl-9--;

col. 26, line 1, "5,10" should read --5,6--;

col. 26, line 62, "of" should read --or--;

col. 27, line 11, "5,10" should read --5,6--;

col. 27, line 12, "dimethyl9" should read --dimethyl-9--;

col. 27, line 12, "[1,2-b]" should read --[2,1-b]--;

col. 27, line 12, "5,10" should read --5,6--;

Signed and Sealed this

Sixth Day of September, 1994

Attest:

BRUCE LEHMAN

Attesting Officer

Commissioner of Patents and Trademarks